United States Patent
Owens et al.

(10) Patent No.: US 10,119,942 B2
(45) Date of Patent: Nov. 6, 2018

(54) MEDIUM-RANGE MAGNETOSTRICTIVE ULTRASONIC GUIDED WAVE SCANNER SYSTEMS AND METHODS

(71) Applicant: FBS, Inc., Bellefonte, PA (US)

(72) Inventors: Steven E. Owens, Bellefonte, PA (US); Cody J. Borigo, Pennsylvania Furnace, PA (US); Joseph L. Rose, State College, PA (US); Borja Lopez, Lynchburg, VA (US)

(73) Assignee: FBS, Inc., Bellefonte, PA (US)

( * ) Notice: Subject to any disclaimer, the term of this patent is extended or adjusted under 35 U.S.C. 154(b) by 397 days.

(21) Appl. No.: 15/043,092

(22) Filed: Feb. 12, 2016

(65) Prior Publication Data
US 2016/0238564 A1    Aug. 18, 2016

Related U.S. Application Data

(60) Provisional application No. 62/116,186, filed on Feb. 13, 2015.

(51) Int. Cl.
*G01N 29/24*       (2006.01)
*G01N 29/265*      (2006.01)

(52) U.S. Cl.
CPC ..... *G01N 29/2412* (2013.01); *G01N 29/2493* (2013.01); *G01N 29/265* (2013.01);
(Continued)

(58) Field of Classification Search
CPC ........... G01N 29/2412; G01N 29/2493; G01N 29/265; G01N 2291/0422; G01N 2291/0425; G01N 2291/2634
(Continued)

(56) References Cited

U.S. PATENT DOCUMENTS 4,027,528 A * 6/1977 Tyree ................... G01N 29/265
                                                      73/620
4,137,470 A   1/1979 Désormière et al.
(Continued)

OTHER PUBLICATIONS

Rose, J.L., Ultrasonic Guided Waves in Solid Media, Cambridge University Press, (2014): 1-15, 269-275.
(Continued)

*Primary Examiner* — Son T Le
*Assistant Examiner* — Tarun Sinha
(74) *Attorney, Agent, or Firm* — Duane Morris LLP

(57) ABSTRACT

An inspection system includes a magnetostrictive scanner probe, a ferromagnetic strip, at least one magnet, and a processor. The magnetostrictive scanner probe includes a probe body for supporting at least one flexible sensor coil and a position encoder. The ferromagnetic strip is configured to be coupled to a structure, and the at least one magnet is configured to apply a biasing magnetization to the ferromagnetic strip. The processor is configured to cause a time-varying current to be generated in the at least one flexible sensor coil to induce a time-varying magnetization in said ferromagnetic strip perpendicular to said biasing magnetization to generate shear horizontal-type guided wave energy into said structure, and process reflected shear horizontal-type guided wave energy received by the at least one flexible sensor coil as the probe is moved relative to said structure to generate at least one two-dimensional image of a region of said structure.

29 Claims, 17 Drawing Sheets

(52) U.S. Cl.
 CPC ............... *G01N 2291/0422* (2013.01); *G01N 2291/0425* (2013.01); *G01N 2291/2634* (2013.01)

(58) Field of Classification Search
 USPC .......................................................... 73/602
 See application file for complete search history.

(56) References Cited

U.S. PATENT DOCUMENTS

| | | |
|---|---|---|
| 4,356,731 A | 11/1982 | Mahony |
| 5,260,615 A | 11/1993 | Sahashi et al. |
| 5,581,037 A | 12/1996 | Kwun et al. |
| 5,821,430 A * | 10/1998 | Kwun ..................... B66B 7/123 73/862.41 |
| 5,841,277 A | 11/1998 | Hedengren et al. |
| 6,148,672 A | 11/2000 | Cawley et al. |
| 6,299,703 B1 | 10/2001 | Chen et al. |
| 6,429,650 B1 | 8/2002 | Kwun et al. |
| 6,624,628 B1 | 9/2003 | Kwun et al. |
| 6,813,950 B2 | 11/2004 | Glascock et al. |
| 6,917,196 B2 | 7/2005 | Kwun et al. |
| 7,375,514 B2 | 5/2008 | Rempt et al. |
| 7,573,261 B1 | 8/2009 | Vinogradov et al. |
| 7,614,313 B2 | 11/2009 | Kim et al. |
| 7,821,258 B2 | 10/2010 | Vinogradov et al. |
| 7,852,073 B2 | 12/2010 | Kwun et al. |
| 7,913,562 B2 | 3/2011 | Kwun et al. |
| 7,997,139 B2 | 8/2011 | Owens et al. |
| 8,354,842 B2 | 1/2013 | Kim et al. |
| 8,653,810 B2 | 2/2014 | Cobb et al. |
| 8,907,665 B2 | 12/2014 | Rose et al. |
| 9,074,995 B2 | 7/2015 | Cho et al. |
| 2002/0105324 A1* | 8/2002 | Kwun ..................... G01N 29/11 324/240 |
| 2006/0055399 A1* | 3/2006 | Georgeson ......... G01N 29/2481 324/232 |
| 2008/0315871 A1* | 12/2008 | Lepage ............... G01N 27/9013 324/242 |
| 2012/0119732 A1* | 5/2012 | Rose ................... G01N 29/2412 324/240 |
| 2015/0329221 A1* | 11/2015 | Georgeson ............ B64F 5/0045 702/36 |
| 2015/0330206 A1* | 11/2015 | Trillon ................... G01N 17/04 138/103 |
| 2016/0299106 A1* | 10/2016 | Khajeh ................ G01N 29/043 |

OTHER PUBLICATIONS

Trémolet de Lacheisserie, E., Magnetostriction: Theory and Applications of Magnetoelasticity, CRC press, (1993): 339-352, 359-361.

Sun, Z., Zhang, L., & Rose, J. L., "Flexural torsional guided wave mechanics and focusing in pipe," Journal of Pressure Vessel Technology, 127.4 (2005): 471-478.

Davies, J. and Cawley, P., "The Application of Synthetic Focusing for Imaging Crack-Like Defects in Pipelines Using Guided Waves," IEEE Transactions on Ultrasonics, Ferroelectrics, and Frequency Control, 56.4 (2009): 759-771.

Sicard, R., Goyette, J., and Zellouf, D., "A SAFT Algorithm for Lamb Wave Imaging of Isotropic Plate-Like Structures," Ultrasonics, 39 (2002):487-494.

Sicard, R., Chahbaz, A., and Goyette, J., "Guided Lamb Waves and L-SAFT Processing Technique for Enhanced Detection and Imaging of Corrosion Defects in Plates with Small Depth-to-Wavelength Ratio," IEEE Transactions on Ultrasonics, Ferroelectrics, and Frequency Control, 51.10 (2004): 1287-1297.

Kuokkala, V.T. and Schwarz, R.B., "The use of magnetostrictive film transducers in the measurement of elastic moduli and ultrasonic attenuation of solids," Rev. Sci. Instrum., 63(5), pp. 3136-3142, 1992.

Joule, J.P., "On the effects of magnetism upon the dimensions of iron and steel bars," Phil. Mag., Series 3, 30(199), pp. 76-87, 1842.

* cited by examiner

MEDIUM-RANGE MAGNETOSTRICTIVE ULTRASONIC GUIDED WAVE SCANNER SYSTEMS AND METHODS

CROSS-REFERENCE TO RELATED APPLICATION(S)

This application claims priority to U.S. Provisional Patent Application No. 62/116,186, filed Feb. 13, 2015, the entirety of which is incorporated by reference herein.

FIELD

The disclosed systems and methods relates to the non-destructive inspection of sections of pipes, plates, and shells using ultrasonic guided waves.

BACKGROUND INFORMATION

Ultrasonic guided wave techniques are utilized in a wide range of non-destructive inspection applications including those for pipes, plates, and shells comprised of metals, composites, and other materials. Guided waves are elastic waves propagating in a bounded structure that is utilized as a waveguide to efficiently transmit one or more wave modes along the structure. One of the foremost benefits of guided waves over other non-destructive inspection techniques is the ability of said waves to propagate over long distances, in many cases hundreds of feet, and to inspect inaccessible or hidden structures from a single probe position.

Long-range guided wave techniques are often utilized for the inspection of pipelines, plates, and shells. However, due to the nature of the guided waves and associated electronics used in such applications, there are inherent limitations of this technology. Two of these limitations are the existence of an uninspectable region, i.e. 'dead zone', around the transducer and a lack of axial and lateral resolution in many applications. Due to these limitations, guided waves are often used as a screening tool for large sections of a structure. However, there exist many opportunities for guided wave applications over short and medium ranges that require greater axial and lateral resolution. Several examples of these opportunities include the detection of corrosion, cracks, and other flaws in close proximity to structural features such as supports, welds, flanges, and air-soil interfaces as well as inspection of short, inaccessible regions such as corrosion under pipe supports (CUPS). The disclosed magnetostrictive ultrasonic guided wave scanner system advantageously yields two-dimensional scan images featuring improved axial and lateral resolution and featuring a small dead zone compared to conventional guided wave inspection systems.

SUMMARY

In some embodiments, a system for non-destructive inspection of a structure includes a magnetostrictive scanner probe, a ferromagnetic strip, at least one magnet, and a processor. The magnetostrictive scanner probe includes a probe body for supporting at least one flexible sensor coil and a position encoder. The ferromagnetic strip is configured to be coupled to the structure, and the at least one magnet is configured to apply a biasing magnetization to the ferromagnetic strip. The processor is configured to cause a time-varying current to be generated in the at least one flexible sensor coil to induce a time-varying magnetization in said ferromagnetic strip perpendicular to said biasing magnetization to generate shear horizontal-type guided wave energy into said structure, and process reflected shear horizontal-type guided wave energy received by the at least one flexible sensor coil as the probe is moved relative to said structure to generate at least one two-dimensional image of a region of said structure.

In some embodiments, a method for non-destructive inspection of a structure is provided. The method includes applying a biasing magnetization to a ferromagnetic strip that is coupled to the structure, moving a scanner probe, which supports at least one sensor coil, relative to said structure along said ferromagnetic strip in a first direction; applying a time-varying current in the at least one sensor coil to induce a time-varying magnetization in said ferromagnetic strip to generate shear horizontal-type guided wave energy into said structure as the scanner probe is moved relative to the structure, the shear horizontal-type guided wave energy propagating through the structure in a second direction; detecting reflected shear horizontal-type guided wave energy as the probe is moved relative to said structure; and processing the reflected shear horizontal-type guided wave energy to generate at least one two-dimensional image of a region of said structure.

DETAILED DESCRIPTION

Figure 1:
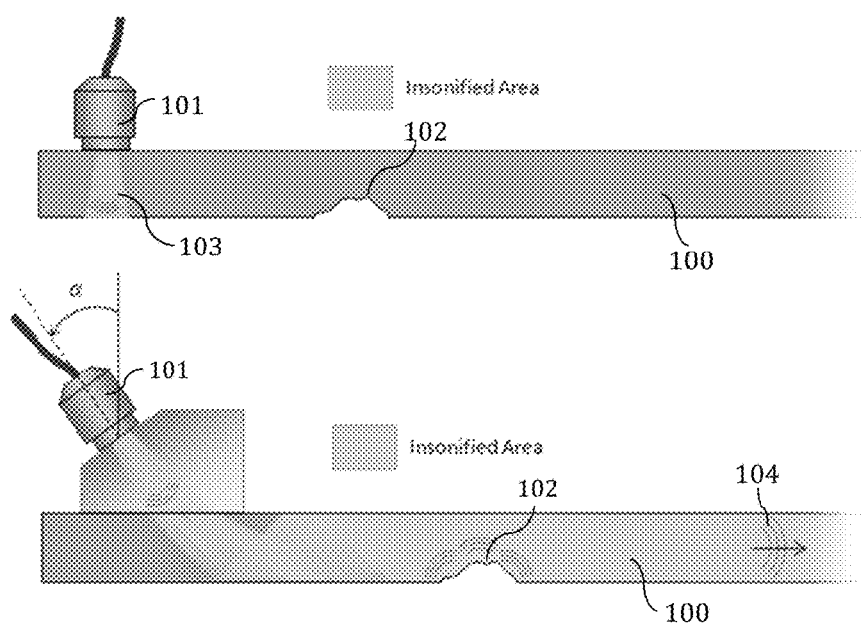
FIG. 1 is a conceptual illustration of the differences between ultrasonic bulk waves and ultrasonic guided waves.

This description of the exemplary embodiments is non-limiting and is intended to be read in conjunction with the accompanying drawings, which are to be considered part of the entire written description.

The disclosed medium-range magnetostrictive ultrasonic guided wave scanner system generates two-dimensional scan images for the purposes of non-destructive inspection of pipes, plates, and shells by sending and receiving shear horizontal-type guided waves in said structures. The system includes at least one pulser/receiver/processor, at least one sensor coil, at least one ferromagnetic strip, at least one biasing magnet, a position encoder, and a probe body upon which at least the coil and encoder are mounted. The pulser/receiver/processor electronics sub-system and software to perform data analysis and hardware control also can be mounted in or on the probe body.

In some embodiments, the sensor coil is a flat flexible cable (FFC), although the sensor coil also can be implemented as a flexible printed circuit board (FPCB) or other flexible structure. The sensor coil can be configured to provide at least one of directional control and wave focusing. The sensor coil may be interchangeable to generate and receive guided waves across a wide range of frequencies between 10 kHz and 2 MHz. In some embodiments, the sensor coil includes at least two separate coil elements that are utilized to achieve at least one of improved focusing, aperture control, directional control, probe calibration, and decreased dead zone extent. The sensor coil may be arranged such that at least one coil element generates the outgoing guided waves and subsequently detects guided wave reflections. Alternatively, the sensor coil may be arranged such that at least one coil element generates the outgoing guided waves and at least one additional coil element detects guided wave reflections.

The bias magnetization of the ferromagnetic material may be achieved by swiping the material with a permanent magnet prior to the scan or by utilizing at least one biasing magnet built into the probe, in which case the magnet magnetizes the ferromagnetic material as the probe is scanned (moved) along the structure. The scanning action of the probe may be achieved by manual or automated means as described in greater detail below.

In some embodiments, the probe body is designed to accommodate structures with a predefined range of curvatures. The probe body may include a coil tensioner device to allow the coil to accommodate structures with a range of curvatures.

A reference target may be coupled to the structure in the region inspected by the scanner at a predetermined distance to act as a probe calibration device and to facilitate defect sizing.

The system includes software configured to perform signal processing techniques to generate and subsequently enhance at least one two-dimensional inspection image. The signal processing techniques utilized in the software include at least one of averaging, filtering, directional wave control, multi-frequency data acquisition, a synthetic aperture focusing technique (SAFT), and time-compensated gain (TCG).

In some embodiments, the system pulser/receiver/processor electronics include at least one ultrasonic tone-burst generator, an analog-to-digital converter, a pre-amplifier, and a controller. The controller includes a non-transitory machine readable storage medium and a processor in signal communication with the non-transitory machine readable storage medium. The processor is configured to cause a pulse to be generated by the at least one magnetostrictive sensor coil, process the reflected signals detected by the at least one magnetostrictive sensor coil, process scanner position data provided by the encoder device, cause the waveform and encoder information to be recorded in the non-transitory machine readable storage medium, and generate at least one two-dimensional scan image of the structure. The two-dimensional scan image of the structure can be output to a display device that is wired or wirelessly coupled to the processor.

The system operates by scanning the probe across at least one strip of a ferromagnetic material that is coupled to a structure. The system generates guided waves via the magnetostrictive effect, by which a time-varying strain is induced in the magnetostrictive material by means of generating a time-varying current in the probe coil in the presence of a biasing magnetization, said biasing magnetization being perpendicular to the direction of wave propagation. The coil traces are oriented in a manner such that they induce a time-varying magnetic field in the ferromagnetic material that is parallel to the wave propagation direction. By this process, shear horizontal-type guided waves are generated in the structure to which the ferromagnetic material is coupled. The shear horizontal-type guided wave modes propagate through the structure away from the probe, and reflected wave energy from any structural anomalies is subsequently detected by the scanner via the inverse magnetostrictive effect. A series of guided wave signals are collected along different sections of the structure and combined into a two-dimensional image in the software by reassembling the individual scans in accordance with the position data associated with each individual scan provided by the encoder device.

Velocity-based calculations are then used to determine the distance of the reflector from the probe. In some embodiments, this process is automatically repeated at a sufficiently high rate as the probe is manually or automatically scanned along the structure to generate a two-dimensional inspection image of a region of the structure, in which the axial and lateral locations and extents of anomalies may be identified.

FIG. 1 provides a conceptual illustration of an ultrasonic transducer 101 used to generate bulk waves 103 and guided waves 104 in a structure 100. Guided waves 104 are formed from the constructive interference of ultrasonic bulk waves 103 that have interacted with the boundaries of the structure 100 in which they propagate. Guided waves are unique in the sense that they are capable of propagating for long distances compared to traditional ultrasonic waves and can be used to inspect hidden/inaccessible structures like buried or cased piping and tubing. Unlike "spot-checking" with traditional ultrasonic techniques, guided waves provide up to a 100% volumetric inspection. Furthermore, guided waves provide an efficient and cost-effective means of inspection due to increased inspection speed and simplicity.

Figure 2:
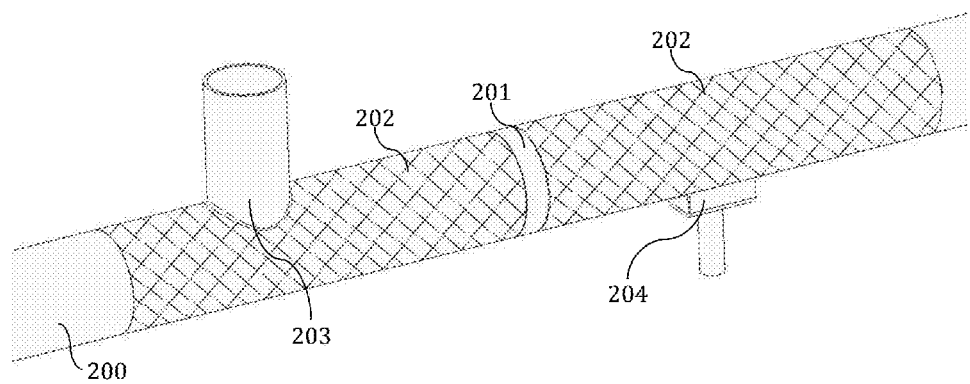
FIG. 2 is an illustration of a complex section of piping with a typical dead zone for a conventional long-range ultrasonic guided wave tool superimposed.

Various means of guided wave transduction exist, including piezoelectric transducers, electromagnetic acoustic transducers (EMATs), impact devices, and magnetostrictive transducers. Magnetostrictive transducers have been utilized for the purposes of ultrasonic guided wave generation, and recently have been utilized for the purposes of long-range pipe inspection in axisymmetric and segmented configurations. FIG. 2 illustrates a conventional long-range guided wave system that can inspect pipelines over distances of up to several hundred feet in each direction from the transducer location 201. However there exists some uninspectable region, i.e. "dead zone" 202, for some distance on each side of the transducer 201. Therefore the application of such systems to pipelines 200 having closely-spaced features such as elbows, flanges, branches 203, supports 204, etc. is impractical. Additionally, the axial and lateral resolution of such systems is generally limited to the order of several inches due to the large wavelengths and limited number of transducer segments utilized in such applications.

Figure 3:
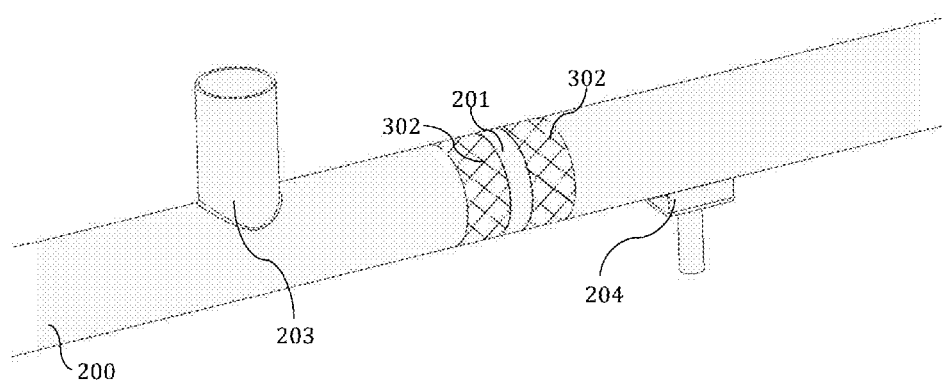
FIG. 3 is an illustration of a complex section of piping with one example of a reduced dead zone that can be achieved using the disclosed system in accordance with some embodiments.

The disclosed medium-range guided wave scanner addresses these issues by integrating a magnetostrictive transducer on a scanner probe that is fitted with an encoder device. This system is capable of generating and detecting shear horizontal-type guided waves with a high signal-to-noise ratio while the probe is scanned along at least one strip of ferromagnetic material coupled to a pipe, plate, shell, or other structure to be inspected. The system automatically correlates the encoder data and the guided wave data to generate a two-dimensional image of reflectors in the inspected area with improved axial and lateral resolution compared to traditional long-range guided wave systems. As illustrated in FIG. 3, the medium-range scanner is able to provide a reduced dead zone 302 (compared to conventional long-range guided wave systems) and to improve the axial and lateral resolution, which allow for the structure 200 to be inspected even with structural features 203 and 204 in close proximity to the transducer location 201.

For the purposes of this description, the term "medium-range" refers to guided wave devices that are capable of scanning a structure up to 20 feet away from the probe location, whereas conventional long-range systems may provide scan data ranging from less than 20' to as much as several hundred feet away from the probe direction depending on the structure, and the term "shear horizontal-type guided waves" refers to torsional waves in cylinders, shear horizontal waves in isotropic plates and shells, and guided wave modes having predominantly in-plane displacement fields perpendicular to the wave propagation direction.

Figure 4:
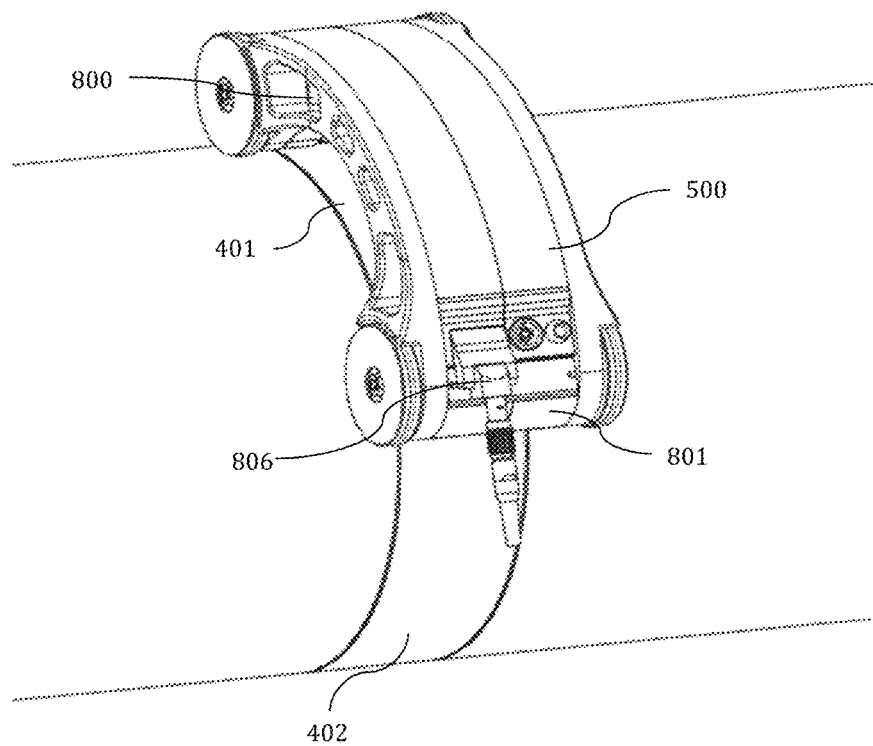
FIG. 4 illustrates one example of a probe applied to a pipe.

FIG. 4 illustrates one example of an improved system in accordance with some embodiments. As shown in FIG. 4, the system includes a probe 400 including a probe body 500 in or on which at least one pulser/receiver sensor coil 401 and at least one biasing magnet 800 are mounted. At least one ferromagnetic strip 402 is coupled to the structure 200 and defines a path along which probe 400 travels. A position encoder 801 is mounted on or within probe body 400 and is configured to provide position information to system electronics, which include a pulser/receiver electronics system and a processor and software to perform data analysis as described in greater detail below.

Figure 5:
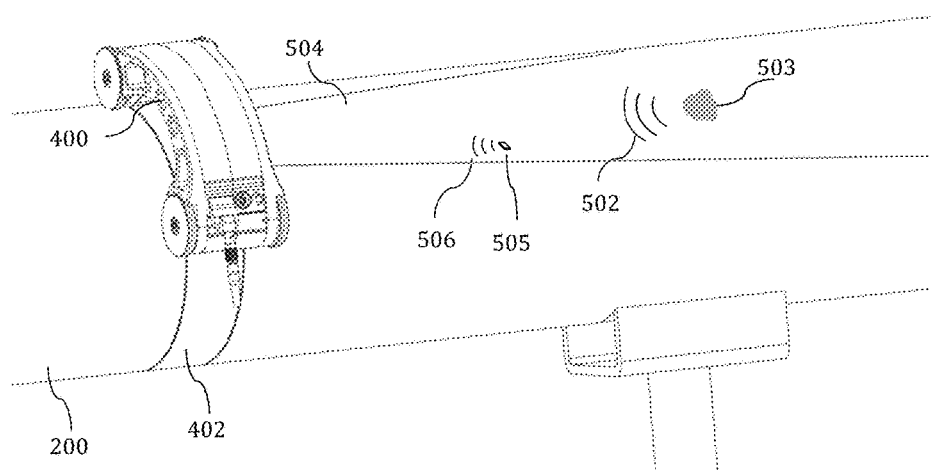
FIG. 5 illustrates one example of a probe detecting reflections from corrosion and a reference target on a pipe using a pulse-echo inspection configuration.

Turning now to FIG. 5, the probe 400 generates guided waves via the magnetostrictive effect by which a time-varying strain is induced in the magnetostrictive material by means of generating a time-varying current in the probe coil 401 in the presence of a biasing magnetic field that is perpendicular to the direction of wave propagation. The coil traces are oriented perpendicular to the wave propagation direction and parallel to the biasing magnetic field and the surface of the structure being investigated such that they induce a time-varying magnetic field in the ferromagnetic material that is parallel to the wave propagation direction. By this process, shear horizontal-type guided waves are generated in the ferromagnetic material and the structure to which the ferromagnetic material is coupled.

As illustrated in FIG. 5, the shear horizontal-type guided wave energy 504 propagates through the structure 200 away from the probe 400, and reflected wave energy 502 from any structural anomalies 503 is subsequently detected by the coil(s) 401 of probe 400 via the inverse magnetostrictive effect. The group velocity of the guided waves is then used to determine the distance of the reflector from the probe 400 based on the arrival time of the reflections and the position data from the encoder 801 is used to determine the lateral (which in some implementations may be circumferential) position of the reflector. This process is automatically repeated as the probe 400 is manually or automatically scanned along the structure to generate a two-dimensional inspection image of a region of the structure 200, from which the axial and lateral locations and extents of anomalies may be identified. The repetition rate of the process must be sufficient to achieve the desired lateral resolution considering the speed of the scanning motion; a typical repetition rate will be between 10 Hz and 10 kHz, although values may fall beyond this range in some circumstances as will be understood by a person of ordinary skill in the art.

In some embodiments, a reference target 505 is coupled to the structure 200 adjacent to the scanner 400 and ferromagnetic strip 402 at a known distance to provide a calibration reference reflection 506 for sizing and system-diagnostics. The reference target may include, but is not limited to, a small metallic block or cylinder that is coupled to the structure 200.

In some embodiments, the sensor coil 401 is a flat flexible cable (FFC) or a flexible printed circuit board (FPCB). The wiring of the FFC or trace design of the FPCB are configured to control the mode and wavelength of the guided waves that are generated and detected by the coil by specifying the periodic spacing of the FFC or FPCB to be approximately equal to one wavelength of the guided waves that are intended to be generated and detected by the device. In both of these embodiments, the flexibility of the sensor coil allows it to conform to a wide range of structural curvature. The sensor coils 401 may be interchangeable to allow the probe to generate and receive guided waves across a wide range of frequencies between 10 kHz and 2 MHz, as well as to achieve one or more of focusing, directional wave control, and aperture control.

In some embodiments, the sensor coil 401 is arranged such that at least one coil element generates the outgoing guided waves and subsequently detects guided wave reflections in a pulse-echo configuration. In alternative embodiments, the sensor coil is arranged such that at least one coil element generates the outgoing guided waves and at least one additional coil element detects guided wave reflections in a pitch-catch configuration. In some embodiments, data is collected at more than one frequency to improve defect detection and inspection confidence.

Figure 6A:
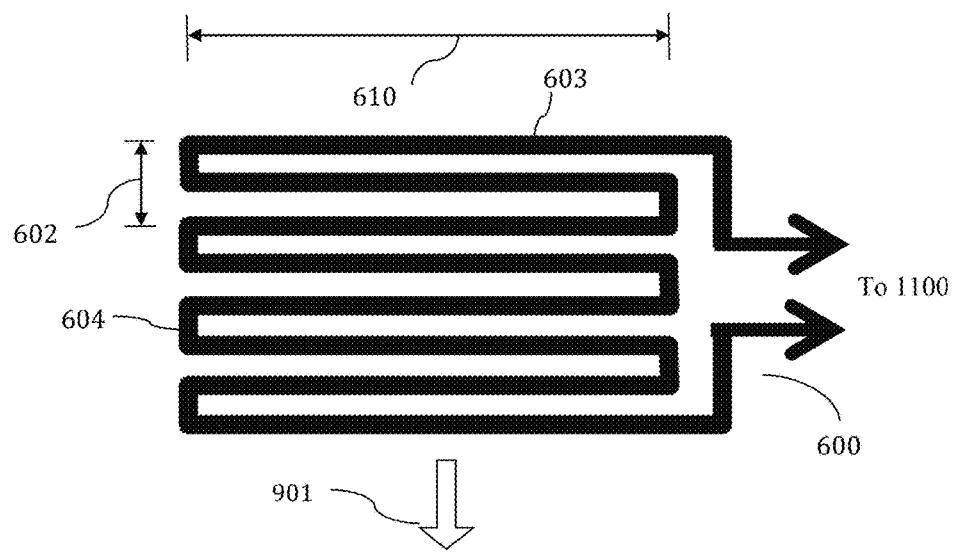
FIGS. 6a and 6b illustrate examples of flexible printed circuit board sensor coils in accordance with some embodiments.

FIG. 6a illustrates one embodiment of a flexible printed circuit board coil 600 without a curvature, but having a predetermined aperture 610. Aperture 610 is the width of the parallel coil traces spaced at a periodic interval 602 and, along with the wavelength of the guided waves, determines the beam divergence angle of the waves emitted from the device. As shown in FIG. 6, coil 600 includes a plurality of straight horizontally extending parallel line segments 603 spaced at periodic interval 602 which is approximately equal to the wavelength of the guided waves that the coil is intended to optimally generate and detect and a plurality of vertically extending line segments 604 connecting line segments 603. The free ends of the circuit traces are connected to the signal generator/receiver 1100 (electronic pulser/receiver system) described in more detail below with respect to FIG. 11.

Figure 6B:
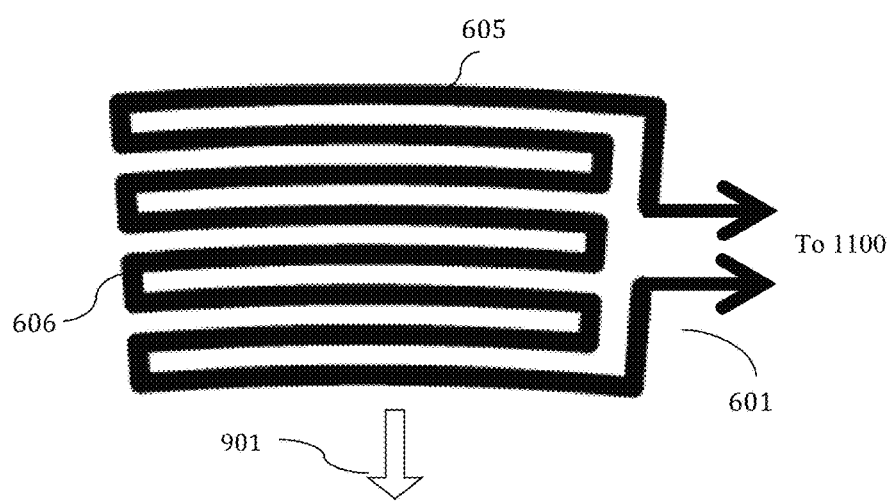

FIG. 6b shows another embodiment of a flexible printed circuit board coil 601. Coil 601 is designed with curvature to focus the guided wave beam as it propagates away from the probe to improve lateral resolution and signal-to-noise ratio. More particularly, the horizontally extending line segments 605 of coil 601 are curved and are connected to each other by a plurality of vertically extending line segments 606.

Figure 7A:
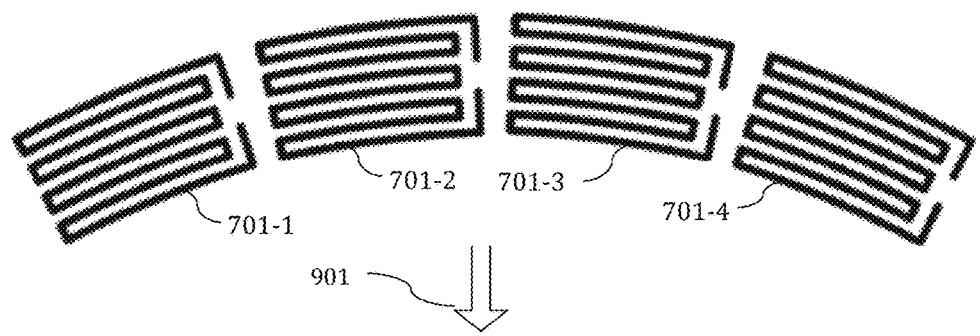
FIGS. 7a-7c are drawings of several embodiments of a set of flexible printed circuit board sensor coils used for beam focusing, improved synthetic aperture focusing, directional control, calibration, and other purposes.

FIG. 7a illustrates an embodiment in which at least two flexible printed circuit board coils 701-1, 701-2, 701-3, 701-4 ("coils 701") are designed to focus the guided wave beam as it propagates away from the probe to improve lateral resolution and signal-to-noise ratio. Although four coils 702 are shown in FIG. 7a, fewer or more coils can be implemented as will be understood by a person of ordinary skill in the art.

Figure 7B:
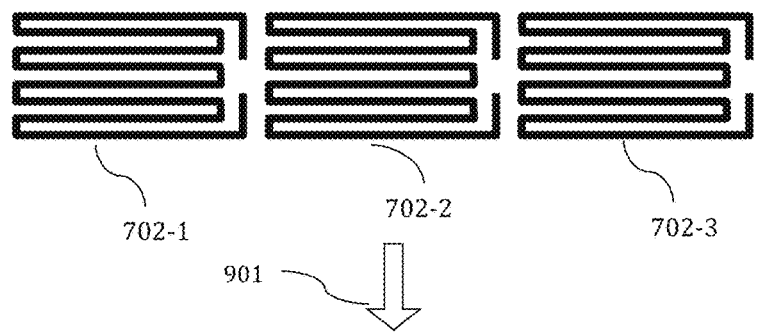

FIG. 7b illustrates another embodiment in which at least two flexible printed circuit board coils 702-1, 702-2, 702-3 ("coils 702") are used as independent pulser and receiver coils for improved synthetic aperture focusing (SAFT) and improved sensitivity to defects that scatter the energy at a large angle. In some embodiments, the segmentation and independent pulser/receiver control of the sensor coils 702 allows for phased array focusing by applying at least one of pre-determined time delays and amplitude factors to the independent coils 702 to focus the energy emitted by the probe.

Figure 7C:
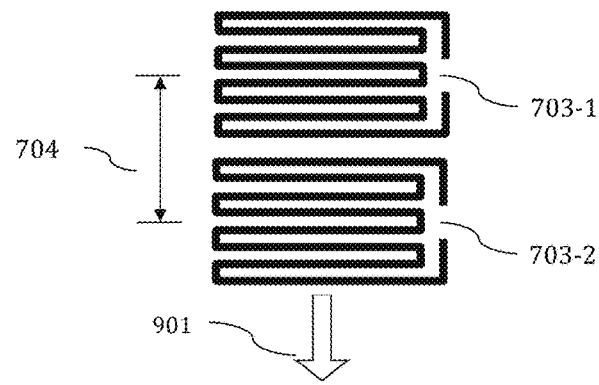

FIG. 7c illustrates another embodiment in which the sensor coil is comprised of at least two separate coil elements 703-1 and 703-2 ("coils 703") that are aligned parallel to the wave propagation direction and separated by some offset 704 that are utilized to calibrate the probe by sending a guided wave between the at least two coil elements 703 while the probe is scanning the structure. The offset 704 is defined as the center-to-center separation distance between the at least two sensor coils and may be such that coils 703 are partially overlapping.

In some embodiments, the at least two separate coil elements 703 are independently controlled and utilized to achieve directional wave control by applying pre-determined time delays based on the phase velocity and frequency of the guided waves and the offset 704 of the coils 703 in order to cancel the forward-propagating or reverse-propagating waves, respectively.

Figure 8A:
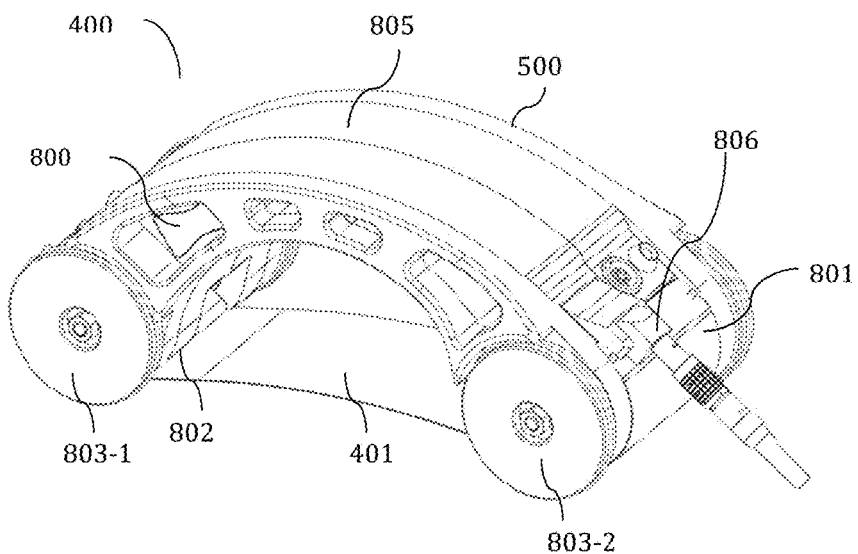
FIGS. 8a-8e illustrate the probe and some of the probe components.

FIG. 8a illustrates the probe 400 in more detail. The probe 400 includes at least a probe body 500, upon which the other components are mounted, a sensor coil 401 that is used to generate and detect the guided waves, a position encoder device 801, which may be internal or external to the device to electronically track the position of the probe 400 on the structure, and at least one biasing magnet 800 and 802. As shown in FIG. 8a, the sensor coil 401 is positioned adjacent to the under portion of probe body 500 and extends from between the front wheels 503-1 to between the rear wheels 503-2 ("wheels 503").

The probe 400 is connected to the pulser/receiver electronics and the controller and microprocessor by means of at least one connector 806. Although a wired connector 806 is shown, a person of ordinary skill in the art will understand that a wireless connection between probe 400 and the electronics can be provided. In some embodiments, an impedance matching network is utilized in conjunction with the sensor coil.

The core 805 of the probe body 500 that is above the sensor coil 401 is composed of a non-conductive material, including but not limited to acetal, HDPE, and ABS plastics, such that it does not interfere with the performance of the magnetostrictive sensor coil 401.

The biasing magnetization of the ferromagnetic strip 402 may be achieved by manually swiping the ferromagnetic strip parallel to the probe scanning direction and perpendicular to the wave propagation direction with a permanent magnet 800, which is shown in FIG. 8a as being temporarily stored in cavity defined in the upper probe body for user convenience. In another embodiment, said biasing magnetization is achieved by a permanent magnet 802 that is integrated into the probe body 500 between the front wheels 803-1 of the probe 400 so that it moves along the surface of said ferromagnetic strip 402 ahead of sensor coil 401 as the probe 400 is scanned along said strip 402.

Figure 8B:
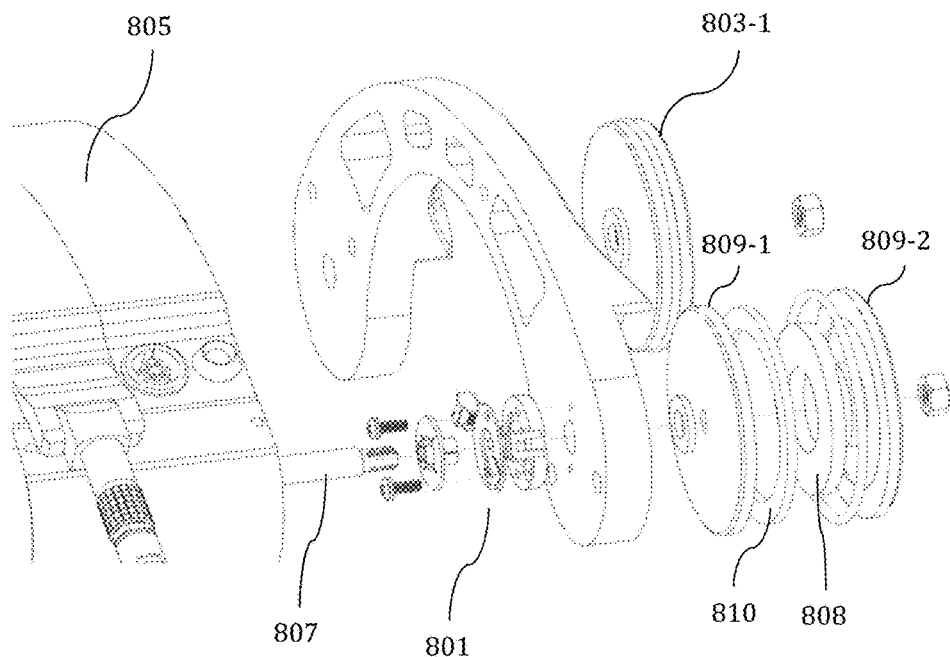

FIG. 8b illustrates some of the internal components of the probe. In some embodiments, the encoder 801 is located within an internal compartment defined by the probe body 500 and is mounted directly to one of the probe axles 807 such that it need not be in direct contact with the structure being scanned. In some embodiments, said encoder 801 can be mounted internally or externally to the probe body 500 such that it is in contact with the structure being scanned. In some embodiments, the wheels 803 are magnetic to maintain contact with the structure being scanned. The magnetic wheels 803 include an inner magnetic core 808, outer wheel plates 809-1 and 809-2 ("wheel plates 809") composed of mildly-magnetic stainless steel and in contact with core 808, and at least one non-magnetic ring 810 between plates 809.

Figure 8C:
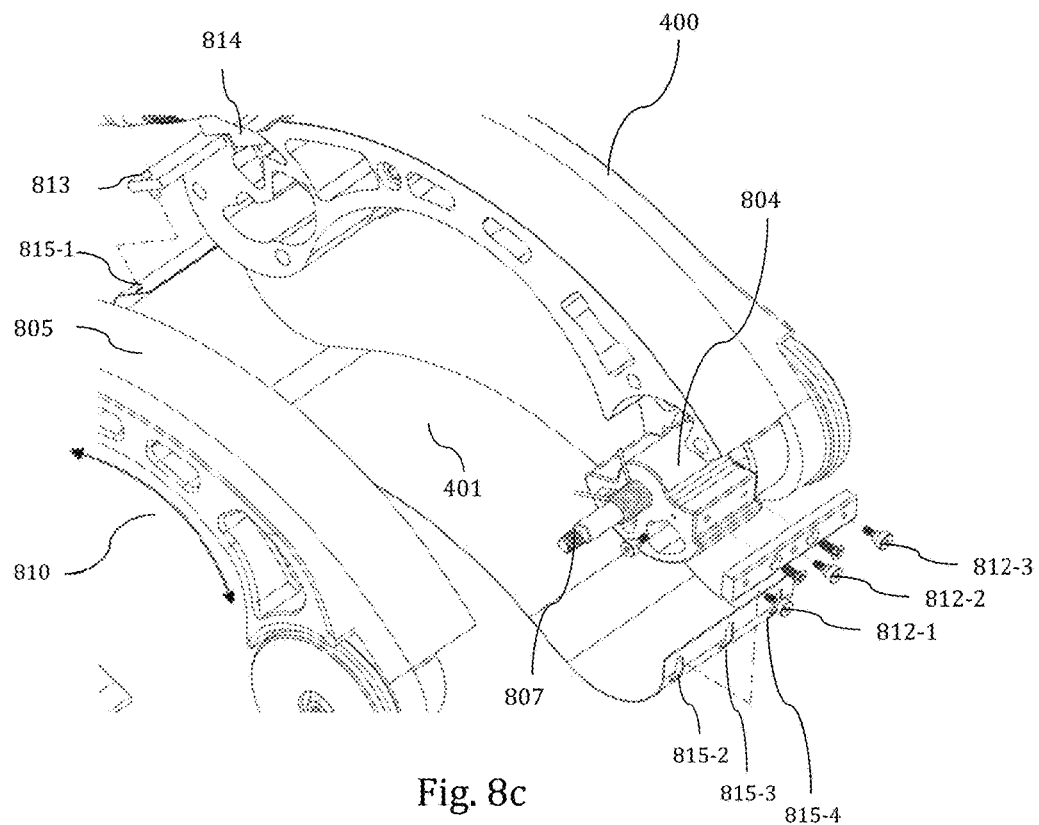
Figure 8D:
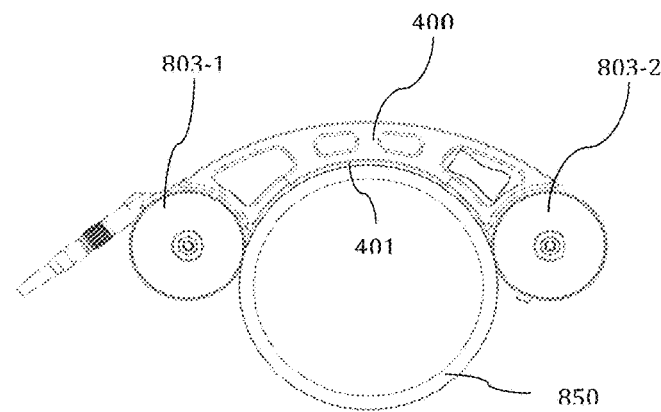
Figure 8E:
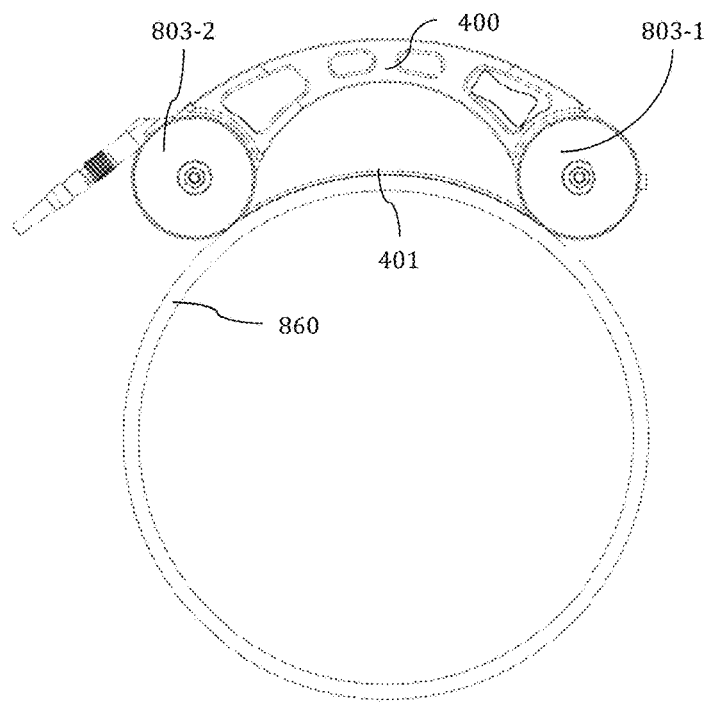

FIGS. 8c-8e illustrate some additional internal components and capabilities of the probe. The probe body 500 is designed with a curvature 810 that allows it to accommodate structures with a predefined range of curvatures in conjunction with coil tensioner 804. This tensioner mechanism 804 works by placing tension on the flexible sensor coil 401 with a cam and torsion spring coil tensioner mechanism 804, which allows the length of the sensor coil 401 in contact with the structure to change according to the radius of curvature of said structure while the wheels 803 remain in contact with said structure. This concept is illustrated for a smaller radius pipe 850 and a larger radius pipe 860 in FIGS. 8d and 8e, respectively. In some embodiments, the probe 400 is designed to accommodate a range of curvatures from 2.25" radius up to flat plates (infinite radius). In some embodiments, the probe 400 is designed to accommodate a range of curvatures from 0.5" radius up to a flat plate (infinite radius).

In some embodiments, the sensor coil 401 is interchangeable to easily facilitate replacement or use of a coil with different functional properties, some examples of which have been described in detail elsewhere in this description. For example and as best seen in FIG. 8c, a set of hooks 812-1, 812-2, and 812-3, a pair of pins 813, corresponding holes 815-1, 815-2, 815-3, and 815-4 ("holes" 815) on said flexible circuit coil 401, and spring-loaded coil capture device 814 facilitate the easy removal and installation of sensor coils without a need for adjusting any fasteners.

Figure 9:
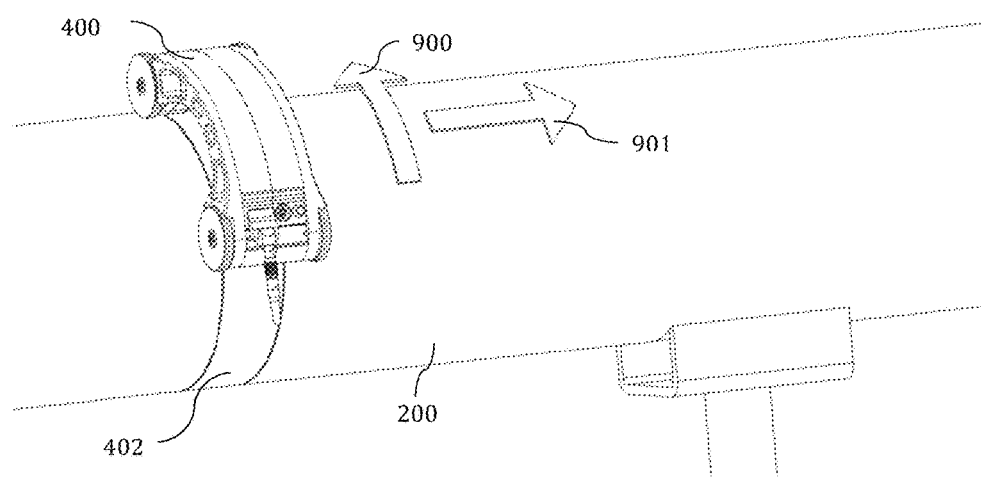
FIG. 9 illustrates one example of the probe being manually scanned around a pipe.

FIG. 9 illustrates the scanning of a structure 200 using probe 400, in which the probe 400 is moved along the ferromagnetic strip 402 in direction 900 parallel to the biasing magnetization direction of said strip and the guided waves are emitted and received in a direction 901 that is generally perpendicular to direction 900.

Figure 10A:
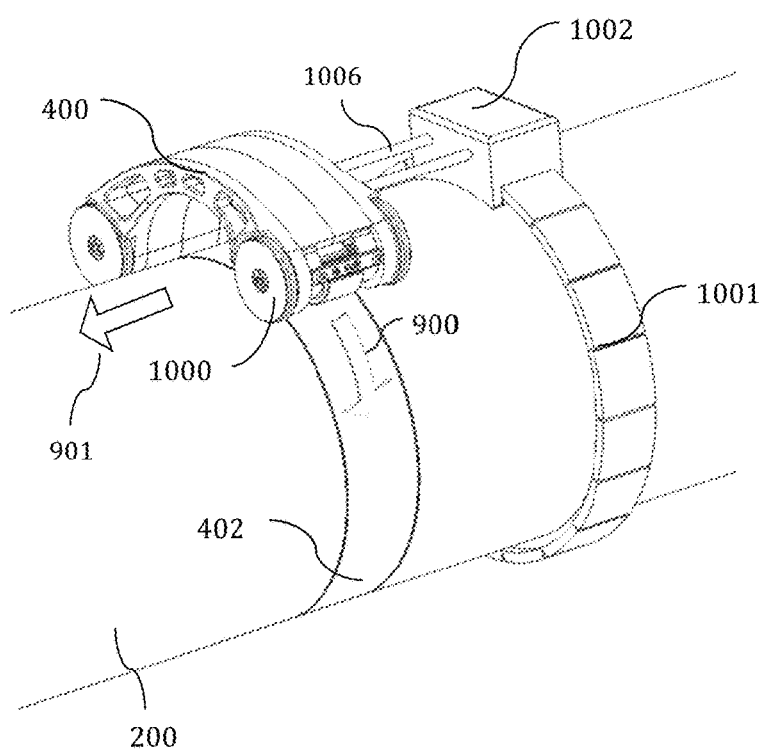
FIGS. 10a-10c are illustrations of several possible embodiments of automated means for scanning the probe along one dimension of a structure.
Figure 10B:
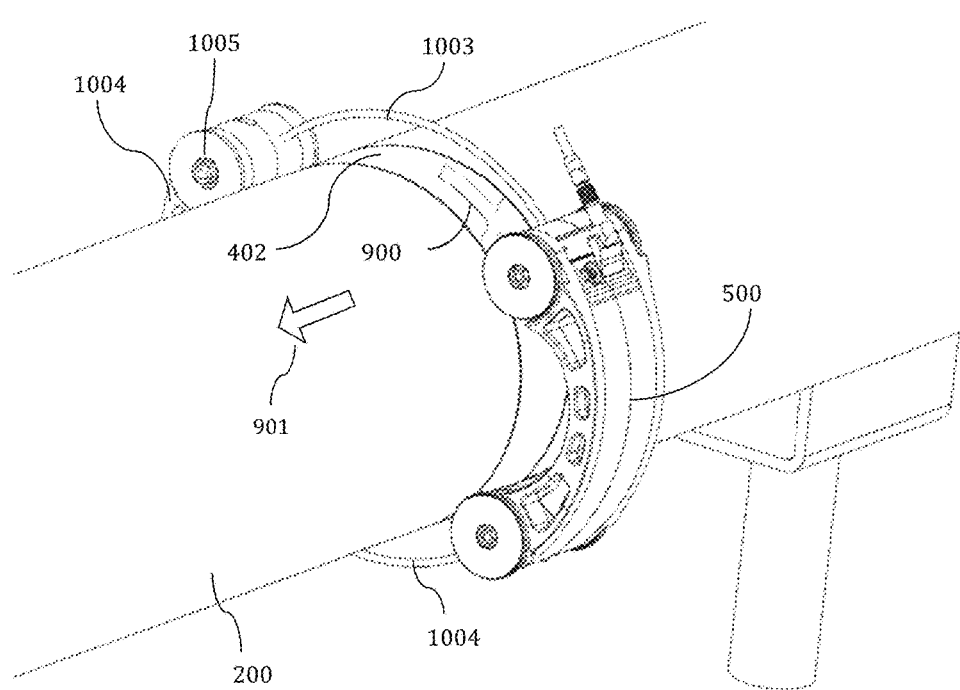
Figure 10C:
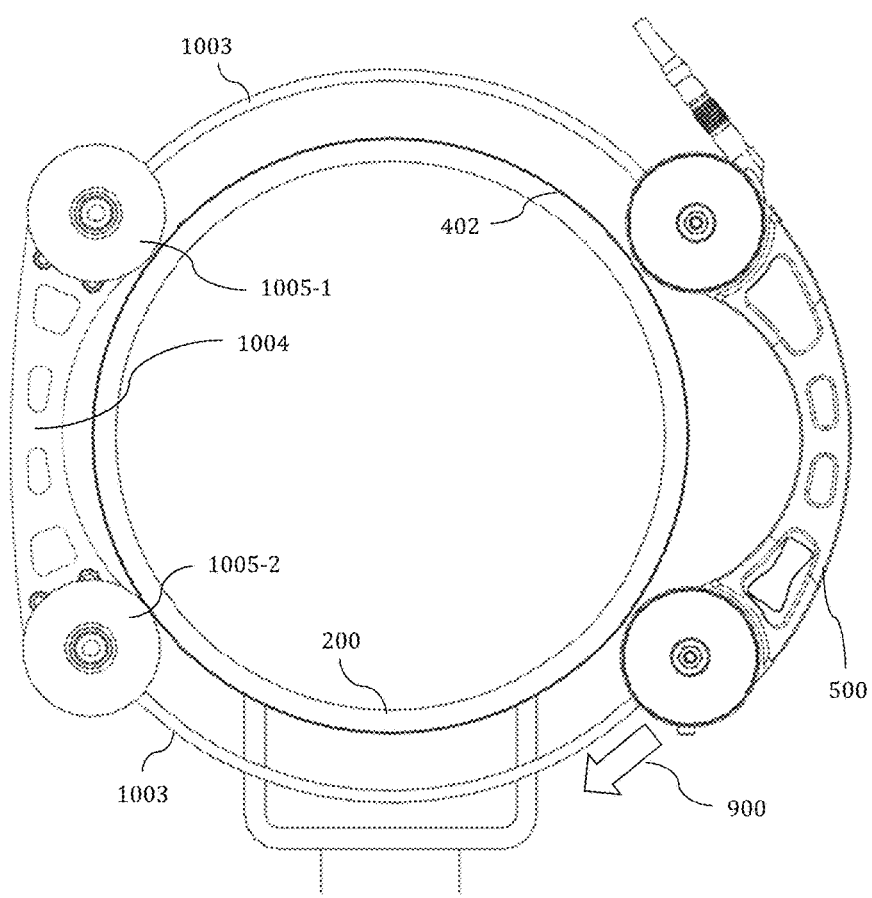

FIGS. 10a-10c illustrate the scanning action 900 of the probe 400 along the ferromagnetic strip 402 that is attached to the structure 200 using one of manual or automated means. As shown in FIGS. 10a-10c, the scanning action 900 is perpendicular to the wave propagation direction 901. As illustrated in FIG. 10a, in some embodiments the automated means of scanning is at least one motorized wheel 1000 attached to the probe 500. In another embodiment illustrated in FIG. 10a, the automated means of scanning is a fixed track system 1001 with a motorized unit 1002 that drives around track 1001 and is rigidly connected to probe 400 via at least one connecting rod 1006.

FIGS. 10b and 10c illustrate another embodiment in which the automated means of scanning is a cable 1003 and motorized tractor 1004 system. In this embodiment, probe 400 has no active drive components, but is connected to motorized tractor unit 1004 via tensioned cables 1003. The cable tension and length can be adjusted to allow the tractor-probe system to be attached to structures with a range of sizes. The tractor unit 1004 is driven by at least one set of motorized wheels 1005-1 and 1005-2 ("wheels 1005"). The automated means of scanning the probe around the structure illustrated in FIGS. 10a-10c are non-limiting, and this description is intended to encompass similar automated means of scanning that would be obvious to those skilled in the art.

Figure 11:
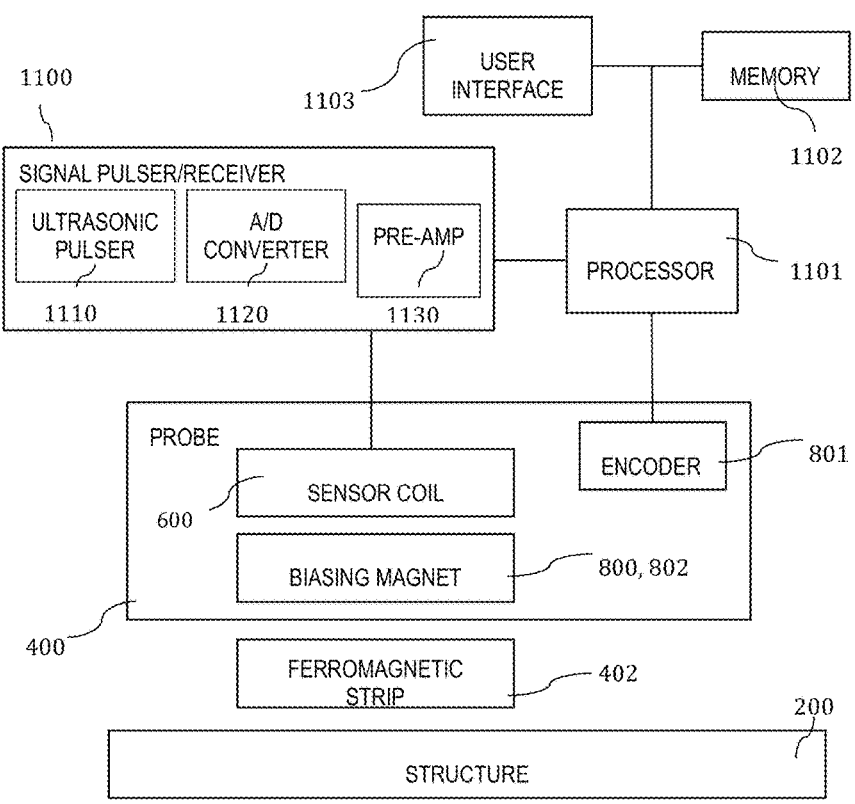
FIG. 11 is a schematic of one embodiment of the system hardware and software.

FIG. 11 provides a schematic illustration of one embodiment of the system. The system includes a processor 1101 in signal communication with the encoder 801, a signal generator/receiver 1100, a memory 1102, and a user interface 1103. User interface 1103 can be implemented using multiple components, including a display, a keyboard, and a mouse. In some embodiments, user interface 1103 is implemented as touch screen display. A person of ordinary skill in the art will understand that a variety of other user interfaces 1103 can be used.

In some embodiments, memory 1102 includes at least one of a read only memory (ROM), random access memory (RAM), a Flash memory, or other non-transitory machine-readable storage medium. Memory 1102 is configured to store software that when executed by processor 1101 controls signal generator/receiver 1100 and performs signal processing techniques to generate and subsequently enhance at least one two-dimensional inspection image. The signal processing techniques utilized in the software may include, but are not limited to, at least one of averaging, filtering, directional wave control, and multi-frequency data acquisition. Other signal processing techniques include synthetic aperture focusing (SAFT), such as disclosed in Sicard et al., "A SAFT algorithm for lamb wave imaging of isotropic plate-like structure" and in Sicard et al., "Guided Lamb Waves and L-SAFT Processing Techniques for Enhanced Detection and Imaging of Corrosion Defects in Plates with Small Depth-to-Wavelength Ratio," both of which are incorporated by reference herein in their entireties, and time-compensated gain (TCG), such as disclosed in U.S. Pat. No. 4,356,731 to Mahoney, which also is incorporated by reference herein in its entirety.

In some embodiments, the signal generator/receiver 1100 includes at least an ultrasonic tone-burst pulser 1110, an analog-to-digital converter 1120, and a pre-amplifier 1130. The processor 1101 and signal generator/receiver 1100 are configured to cause a pulse to be generated by the at least one magnetostrictive coil 600, process the reflected signals detected by the at least one magnetostrictive coil 600, process scanner position data provided by the encoder device 801, and record the waveform and encoder information in the machine readable storage medium 1102.

Figure 12:
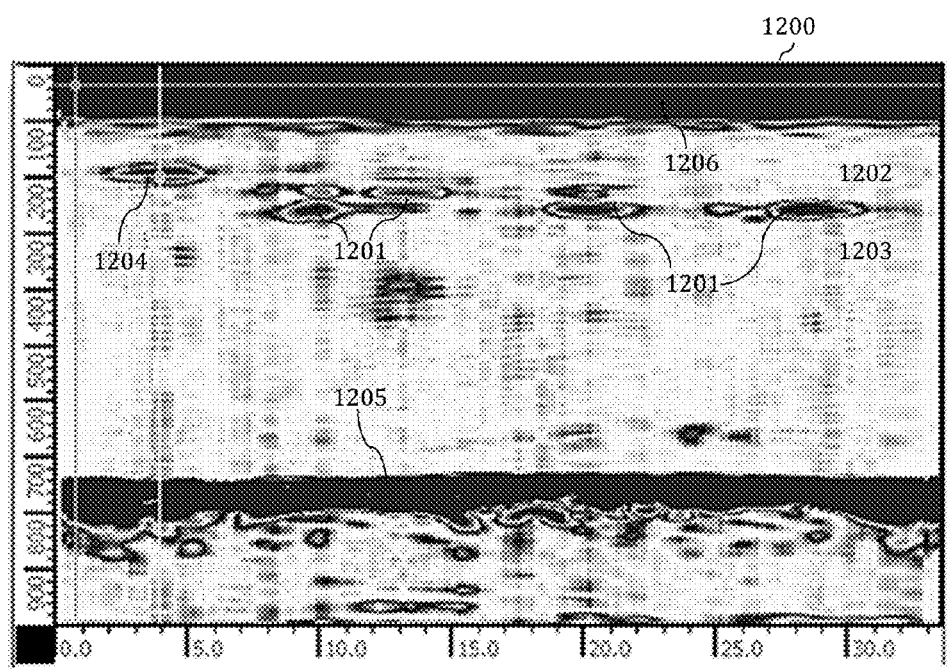
FIG. 12 is a two-dimensional scan image of a 10"-diameter pipe with pitting corrosion on both sides of a cylindrical-style support.

FIG. 12 shows a two-dimensional scan image 1200 of pitting corrosion 1201 around a spider-style pipe support on a 10" fuel pipeline. The regions of pitting on the near side 1202 and far side 1203 of the support are identifiable, as is a reference target 1204 and the cut end 1205 of the pipe section. In this case, the dead zone 1206 is approximately 6", but much shorter dead zones can be realized by the disclosed systems and methods.

Figure 13:
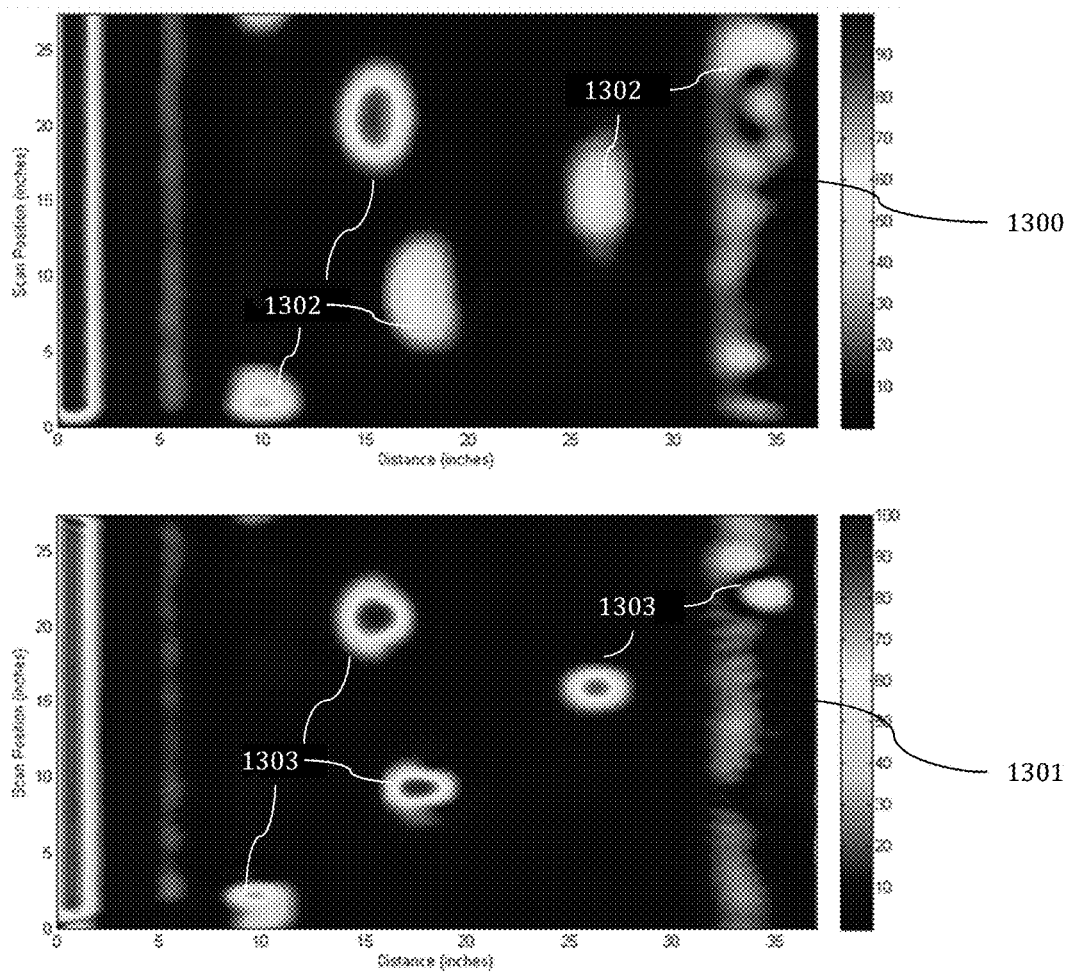
FIG. 13 is a comparison of two-dimensional scan images of an 8"-diameter pipe with a series of defects with (bottom) and without (top) the application of a synthetic aperture focusing (SAFT) algorithm.

One example of the effect of a synthetic aperture focusing technique (SAFT) algorithm is provided in FIG. 13. In embodiments in which a SAFT algorithm is utilized, a time- or frequency-domain algorithm is employed to correlate the reflections detected from various probe locations to reduce the effective beam width of the probe and improve angular resolution. In this case, the image 1301 with SAFT shows circumferentially narrower defect indications 1303 than the same defect reflections 1302 in the image 1300 without SAFT processing.

In some embodiments, a system for non-destructive inspection of a structure includes a magnetostrictive scanner probe, a ferromagnetic strip, at least one magnet, and a processor. The magnetostrictive scanner probe includes a probe body for supporting at least one flexible sensor coil and a position encoder. The ferromagnetic strip is configured to be coupled to the structure, and the at least one magnet is configured to apply a biasing magnetization to the ferromagnetic strip. The processor is configured to cause a time-varying current to be generated in the at least one flexible sensor coil to induce a time-varying magnetization in said ferromagnetic strip perpendicular to said biasing magnetization to generate shear horizontal-type guided wave energy into said structure, and process reflected shear horizontal-type guided wave energy received by the at least one flexible sensor coil as the probe is moved relative to said structure to generate at least one two-dimensional image of a region of said structure.

In some embodiments, the at least one flexible sensor coil comprises a flat flexible cable.

In some embodiments, the at least one flexible sensor coil comprises a flexible printed circuit board.

In some embodiments, the at least one flexible sensor coil is sized and configured to focus the guided wave energy as the guided wave energy propagates away from the magnetostrictive scanner probe.

In some embodiments, the at least one flexible sensor coil includes at least two sensor coils. The at least two flexible sensor coils are supported by the probe body such that they are arranged perpendicular to the wave propagation direction.

In some embodiments, the processor is configured to cause at least one of time delays and amplitude factors to the at least two flexible sensor coils to focus the guided wave energy as it propagates away from the probe.

In some embodiments, the at least one flexible sensor coil is interchangeable without the need to adjust fasteners.

In some embodiments, the at least one flexible sensor coil includes at least two sensor coils. The at least two flexible sensor coils are supported by the probe body such that they are arranged parallel to the wave propagation direction. The processor is configured to cause pre-determined time delays to pulses applied to the at least two flexible sensor coils for suppressing forward- or reverse-propagating waves from the probe.

In some embodiments, the at least one flexible sensor coil is configured to transmit guided wave energy to at least one other sensor coil to perform probe calibration.

In some embodiments, the at least one flexible sensor coil is configured to transmit guided wave energy and subsequently detect guided wave reflections.

In some embodiments, the at least one flexible sensor coil is configured to transmit guided wave energy and at least one other sensor coil detects guided wave reflections.

In some embodiments, the probe body is configured to accommodate structures with a predefined range of curvatures.

In some embodiments, the inspection system includes a coil tensioner device coupled to the at least one flexible sensor coil and supported by the probe body for adjusting a tension of the at least one flexible sensor coil.

In some embodiments, the at least one magnet is coupled permanently to the probe body such that the at least one magnet induces said magnetization as the probe body is scanned along said ferromagnetic strip.

In some embodiments, the at least one magnet is separable from the probe body and is sized and configured to be manually swiped along the ferromagnetic strip prior to scanning.

In some embodiments, the probe body defines an opening for supporting the at least one magnet.

In some embodiments, magnetic wheels are coupled to the probe body to assist in maintaining the probe body in contact with the structure.

In some embodiments, a motor is provided for causing wheels coupled to the probe body to rotate and move the probe body along the structure.

In some embodiments, the inspection system includes a track and motorized unit connected to the probe body for moving the probe body along the structure.

In some embodiments, the inspection system includes a tensioned cable and tractor system connected to the probe for moving the probe body along the structure.

In some embodiments, a method for non-destructive inspection of a structure is provided. The method includes applying a biasing magnetization to a ferromagnetic strip that is coupled to the structure, moving a scanner probe, which supports at least one sensor coil, relative to said structure along said ferromagnetic strip in a first direction; applying a time-varying current in the at least one sensor coil to induce a time-varying magnetization in said ferromagnetic strip to generate shear horizontal-type guided wave energy into said structure as the scanner probe is moved relative to the structure, the shear horizontal-type guided wave energy propagating through the structure in a second direction; detecting reflected shear horizontal-type guided wave energy as the probe is moved relative to said structure; and processing the reflected shear horizontal-type guided wave energy to generate at least one two-dimensional image of a region of said structure.

In some embodiments, a method includes coupling the ferromagnetic strip to the structure, and placing the scanner probe on the structure adjacent to the ferromagnetic strip.

In some embodiments, the first direction is perpendicular to the second direction.

In some embodiments, a method includes coupling a reference target to the structure, and performing a calibration routine using shear horizontal-type guided wave energy reflected from the reference target.

In some embodiments, the scanner probe is move manually, and in some embodiments, the scanner probe includes using a motor.

In some embodiments, processing the reflected shear horizontal-type guided wave energy includes amplifying the reflected shear horizontal-type guided wave energy to produce an amplified signal, and converting the amplified signal from an analog signal to a digital signal using an analog-to-digital converter.

In some embodiments, the processing includes using known wave velocity and probe position data to generate the at least one two-dimensional image of the region.

In some embodiments, the processing includes using a synthetic aperture focusing technique to generate the at least one two-dimensional image of the region.

The ultrasonic guided wave scanner systems and associated methods disclosed herein advantageously provide for reduced dead zones and improved axial and lateral resolutions compared to conventional guided wave systems. As such, the disclosed systems and methods advantageously enable the inspection of structures having closely-spaced features, such as elbows, flanges, branches, and supports, with improved axial and lateral resolutions compared to conventional systems.

In some embodiments, at least a portion of the disclosed methods can be embodied in the form of methods and systems for practicing those methods. Further, the disclosed systems and methods also can be embodied in the form of program code embodied in tangible media, such as floppy diskettes, CD-ROMs, DVD-ROMs, Blu-ray disks, hard drives, or any other non-transitory machine-readable storage medium, wherein, when the program code is loaded into and executed by a machine, such as a processor, the processor becomes an apparatus for practicing the invention. When implemented on a general-purpose processor, the program code segments combine with the processor to provide a unique device that operates analogously to specific logic circuits.

Although the disclosed systems and methods have been described in terms of exemplary embodiments, they are not limited thereto. Rather, the appended claims should be construed broadly, to include other variants and embodiments of the systems and methods, which may be made by those skilled in the art without departing from the scope and range of equivalents of the systems and methods.

What is claimed is:

1. A system for non-destructive inspection, comprising:
  a magnetostrictive scanner probe including a probe body for supporting at least one flexible sensor coil, a coil tensioner device, at least one wheel, and a position encoder, wherein the coil tensioner device is configured to adjust a tension of the at least one flexible sensor coil to adapt the at least one flexible sensor coil to a curvature of a structure to be inspected, and wherein the at least one wheel is configured to be disposed on a surface of the structure to be inspected for moving the probe body relative to the structure to be tested;
  a ferromagnetic strip configured to be coupled to the structure to be inspected;
  at least one magnet for applying a biasing magnetization to the ferromagnetic strip; and
  a processor configured to
    cause a time-varying current to be generated in the at least one flexible sensor coil to induce a time-varying magnetization in said ferromagnetic strip perpendicular to said biasing magnetization to generate shear horizontal-type guided wave energy into said structure to be inspected, and
    process reflected shear horizontal-type guided wave energy received by the at least one flexible sensor coil as the probe is moved relative to said structure to be inspected to generate at least one two-dimensional image of a region of said structure to be inspected.

2. The system of claim 1, wherein the at least one flexible sensor coil comprises a flat flexible cable.

3. The system of claim 1, wherein the at least one flexible sensor coil comprises a flexible printed circuit board.

4. The system of claim 3, wherein the at least one flexible sensor coil is sized and configured to focus the shear horizontal-type guided wave energy as the shear horizontal-type guided wave energy propagates away from the magnetostrictive scanner probe.

5. The system of claim 3, wherein the at least one flexible sensor coil includes at least two sensor coils, the at least two flexible sensor coils supported by the probe body such that they are arranged perpendicular to a direction in which the shear horizontal-type guided wave energy propagates.

6. The system of claim 5, wherein processor is configured to cause at least one of time delays and amplitude factors to the at least two flexible sensor coils to focus the shear horizontal-type guided wave energy as it propagates away from the probe.

7. The system of claim 3, wherein the at least one flexible sensor coil is interchangeable without the need to adjust fasteners.

8. The system of claim 1, wherein the at least one flexible sensor coil includes at least two sensor coils, the at least two flexible sensor coils supported by the probe body such that they are arranged parallel to a direction in which the shear horizontal-type guided wave energy propagates, and wherein the processor is configured to cause pre-determined time delays to pulses applied to the at least two flexible sensor coils for suppressing forward- or reverse-propagating waves from the probe.

9. The system of claim 1, wherein the at least one flexible sensor coil is configured to transmit guided wave energy to at least one other sensor coil to perform probe calibration.

10. The system of claim 1, wherein the at least one flexible sensor coil is configured to transmit guided wave energy and subsequently detect guided wave reflections.

11. The system of claim 1, wherein the at least one flexible sensor coil is configured to transmit guided wave energy and at least one other sensor coil detects guided wave reflections.

12. The system of claim 1, wherein the probe body is configured to accommodate structures with a predefined range of curvatures.

13. The system of claim 1, wherein the at least one magnet is coupled permanently to the probe body such that the at least one magnet induces said magnetization as the probe body is scanned along said ferromagnetic strip.

14. The system of claim 1, wherein the at least one magnet is separable from the probe body and is sized and configured to be manually swiped along the ferromagnetic strip prior to scanning.

15. The system of claim 14, wherein the probe body defines an opening for supporting the at least one magnet.

16. The system of claim 1, wherein the at least one wheel includes a plurality of magnetic wheels.

17. The system of claim 1, further comprising a motor for causing wheels coupled to the probe body to rotate and move the probe body along the structure.

18. The system of claim 1, further comprising a track and motorized unit connected to the probe body for moving the probe body along the structure.

19. The system of claim 1, further comprising a tensioned cable and tractor system connected to the probe for moving the probe body along the structure.

20. A method for non-destructive inspection of a structure, comprising:
applying a biasing magnetization to a ferromagnetic strip that is coupled to the structure such that the ferromagnetic strip extends at least partially around a circumference of the structure;
moving a scanner probe in a first direction relative to said structure along said ferromagnetic strip that extends at least partially around the circumference of the structure, the scanner probe supporting at least one sensor coil and an encoder;
applying a time-varying current in the at least one sensor coil to induce a time-varying magnetization in said ferromagnetic strip to generate shear horizontal-type guided wave energy into said structure as the scanner probe is moved in the first direction relative to the structure, the shear horizontal-type guided wave energy propagating through the structure in a second direction that is different from the first direction;
detecting reflected shear horizontal-type guided wave energy as the probe is moved relative to said structure; and
processing the reflected shear horizontal-type guided wave energy and positional data received from the encoder to generate at least one two-dimensional image of a region of said structure.

21. The method of claim 20, further comprising:
coupling the ferromagnetic strip to the structure; and
placing the scanner probe on the structure adjacent to the ferromagnetic strip.

22. The method of claim 20, wherein the first direction is perpendicular to the second direction.

23. The method of claim 20, further comprising:
coupling a reference target to the structure; and
performing a calibration routine using shear horizontal-type guided wave energy reflected from the reference target.

24. The method of claim 20, wherein moving the scanner probe is done manually.

25. The method of claim 20, wherein moving the scanner probe includes using a motor.

26. The method of claim 20, wherein processing the reflected shear horizontal-type guided wave energy includes
amplifying the reflected shear horizontal-type guided wave energy to produce an amplified signal; and
converting the amplified signal from an analog signal to a digital signal using an analog-to-digital converter.

27. The method of claim 20, wherein the processing includes using known wave velocity and probe position data to generate the at least one two-dimensional image of the region.

28. The method of claim 20, wherein the processing includes using a synthetic aperture focusing technique to generate the at least one two-dimensional image of the region.

29. A system for non-destructive inspection of a structure, comprising:
a magnetostrictive scanner probe including a probe body for supporting at least one flexible sensor coil and a position encoder;
a ferromagnetic strip configured to be coupled to the structure;
at least one magnet for applying a biasing magnetization to the ferromagnetic strip; and
a processor configured to
cause a time-varying current to be generated in the at least one flexible sensor coil to induce a time-varying magnetization in said ferromagnetic strip perpendicular to said biasing magnetization to generate shear horizontal-type guided wave energy into said structure, and
process reflected shear horizontal-type guided wave energy received by the at least one flexible sensor coil as the probe is moved relative to said structure to generate at least one two-dimensional image of a region of said structure;
wherein the at least one flexible sensor coil includes at least two flexible sensor coils, the at least two flexible sensor coils supported by the probe body such that they are arranged parallel to a direction in which the shear horizontal-type guided wave energy propagates, and wherein the processor is configured to cause pre-determined time delays to pulses applied to the at least two flexible sensor coils for suppressing forward- or reverse-propagating waves from the probe.

* * * * *